United States Patent [19]

Senturia et al.

[11] 4,423,371

[45] Dec. 27, 1983

[54] METHODS AND APPARATUS FOR MICRODIELECTROMETRY

[75] Inventors: Stephen D. Senturia, Boston; Steven L. Garverick, Acton, both of Mass.

[73] Assignee: Massachusetts Institute of Technology, Cambridge, Mass.

[21] Appl. No.: 299,264

[22] Filed: Sep. 3, 1981

[51] Int. Cl.³ .............................................. G01R 27/02
[52] U.S. Cl. .................................. 324/61 R; 324/65 R; 357/23
[58] Field of Search ............... 324/57 R, 61 R–62, 324/65 R; 357/25, 23 MG, 17; 29/574, 578, 579

[56] References Cited

U.S. PATENT DOCUMENTS 3,882,381  5/1975  Gregory .................... 324/65 R X
4,158,807  6/1979  Senturia .................. 357/23 MG X
4,316,140  2/1982  Senturia .................. 357/23 MG X

OTHER PUBLICATIONS

Garverick et al.: "An MOS Device . . . Moisture Monitoring"—IEEE Tran. Electron Devices–Jan. 1982, pp. 90–94.

Primary Examiner—Stanley T. Krawczewicz
Assistant Examiner—Jose M. Solis
Attorney, Agent, or Firm—Arthur A. Smith, Jr.; Thomas J. Engellenner

[57] ABSTRACT

An impedance measuring apparatus having a measuring transistor with its gate electrode adapted to form a two electrode, interdigitated capacitor with the material to be measured forming the dielectric, a second reference transistor connected in differential configuration to the measuring transistor so that their drain currents are constrained to be equal, a time-varying voltage generator connected to one electrode of the interdigitated capacitor and a gain-phase meter connected to the gate of the reference transistor.

2 Claims, 8 Drawing Figures

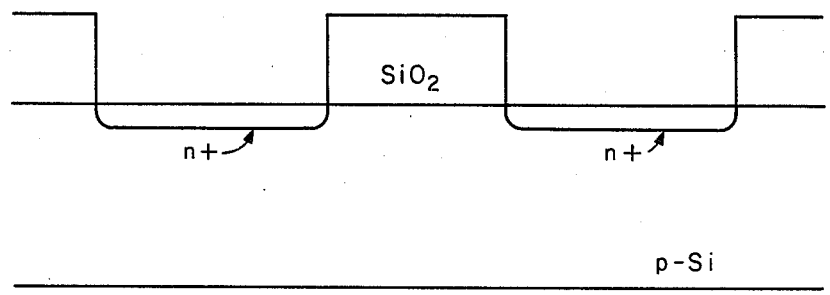
FIG. 4a WAFER CROSS SECTION FOLLOWING ARSENIC IMPLANT
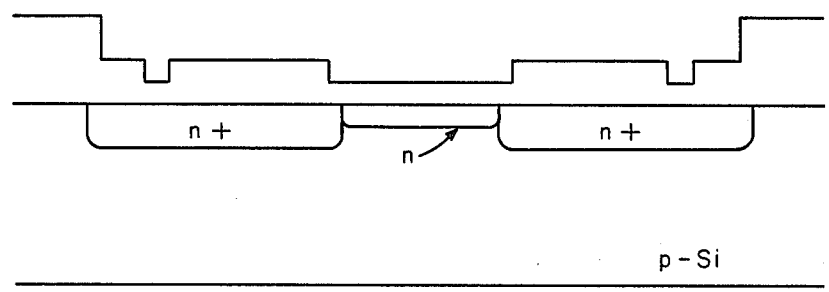
FIG. 4b WAFER CROSS SECTION FOLLOWING PHOSPHORUS IMPLANT
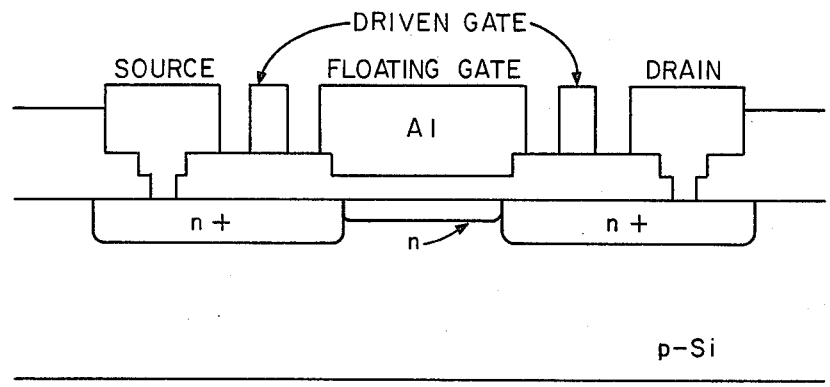
FIG. 4c WAFER CROSS SECTION OF COMPLETED DEVICE

METHODS AND APPARATUS FOR MICRODIELECTROMETRY

The U.S. government has rights in this invention pursuant to Office of Naval Research Contract N00014-78-C0591.

TECHNICAL FIELD

This invention concerns field effect transistors and, in particular, field effect transistors and auxilliary apparatus for measuring the curing and other properties of high-impedence resinous materials.

BACKGROUND

Various methods are known for measuring the cure of resinous materials. For example, colorimetry, spectroscopy and torsional braid analysis provide thermal, chemical and mechanical analyses of resins; however, these techniques are laboratory tests and are not suitable for on-line production monitoring. Dielectrometry, i.e. metal foils imbedded in parts during manufacture and excited by A.C. currents in the range of 100 Hz to 100 kHz, provides for on-line testing, but results, to date, have failed to provide reliable cure monitoring data.

There exists a need for a reliable, inexpensive, resin cure monitor which is sensitive to the test material's dielectric property changes and which can be implanted during manufacture and be suitable for on-line testing. Preferably the apparatus should also be adaptable to measure other properties of the test materials, such as moisture content, as well. Attention is directed to a master's thesis by S. L. Gaverick, an inventor herein, entitled "A.C. Measurements with a Depletion-Mode Charge-Flow Transistor" submitted to Massachusetts Institute of Technology in September, 1980, incorporated herein by reference.

SUMMARY OF THE INVENTION

We have discovered a device and associated measurement technique that can be used to make A.C. measurements in frequency range of less than 1 Hz to about 10 kHz and yield highly reliable data on curing and other material properties.

Our basic device can take the form of an integrated circuit fabricated on a silicon chip. The device combines a planar interdigitated capacitor with a field-effect transistor which serves to amplify the small currents coupled through the interdigitated capacitor when driven with sinusoidal signals. A second field-effect transistor on the chip serves as an electronic reference to compensate the effects of temperature changes. Using these devices, the dielectric properties of the medium in which the chip is placed can be monitored continuously. As a result of the built-in amplification, frequencies as low as 1 Hz can be used. We have found that the low-frequency data in resin-cure studies contains much more detail than can be observed at frequencies in the 1000 Hz range used in conventional dielectrometry.

BRIEF DESCRIPTION OF THE FIGURES

FIGS. 4a-4c are schematic diagrams of the fabrication of our devices;

DESCRIPTION OF THE PREFERRED EMBODIMENT

Figure 1:
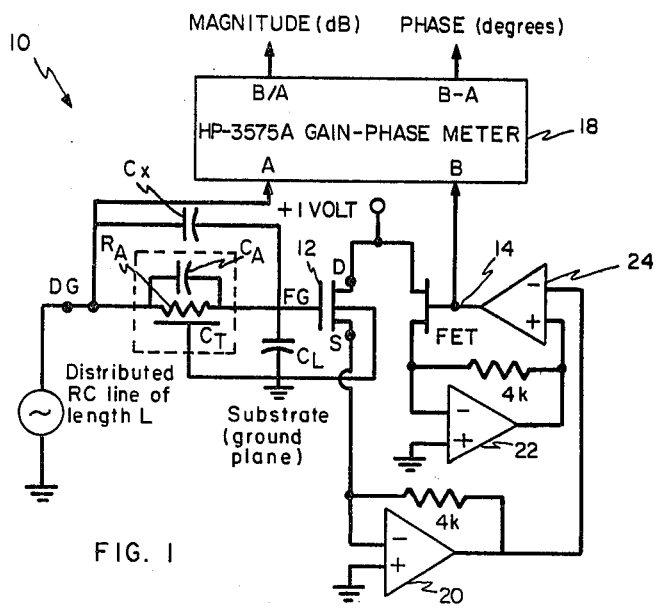
FIG. 1 is a schematic diagram of the measuring apparatus of our invention.

In FIG. 1 our apparatus 10 is shown, comprising a measuring transistor 12 and a reference transistor 14, the two transistors being connected in a differential configuration by components 20, 22 and 24 and arranged such that their drain currents are constrained to be equal. The apparatus also comprises a means 16 to introduce a time-varying voltage function and a means 18 to determine the impedance of the material under measurement by comparing the reference transistor's gate voltage with the input voltage.

Figure 2:
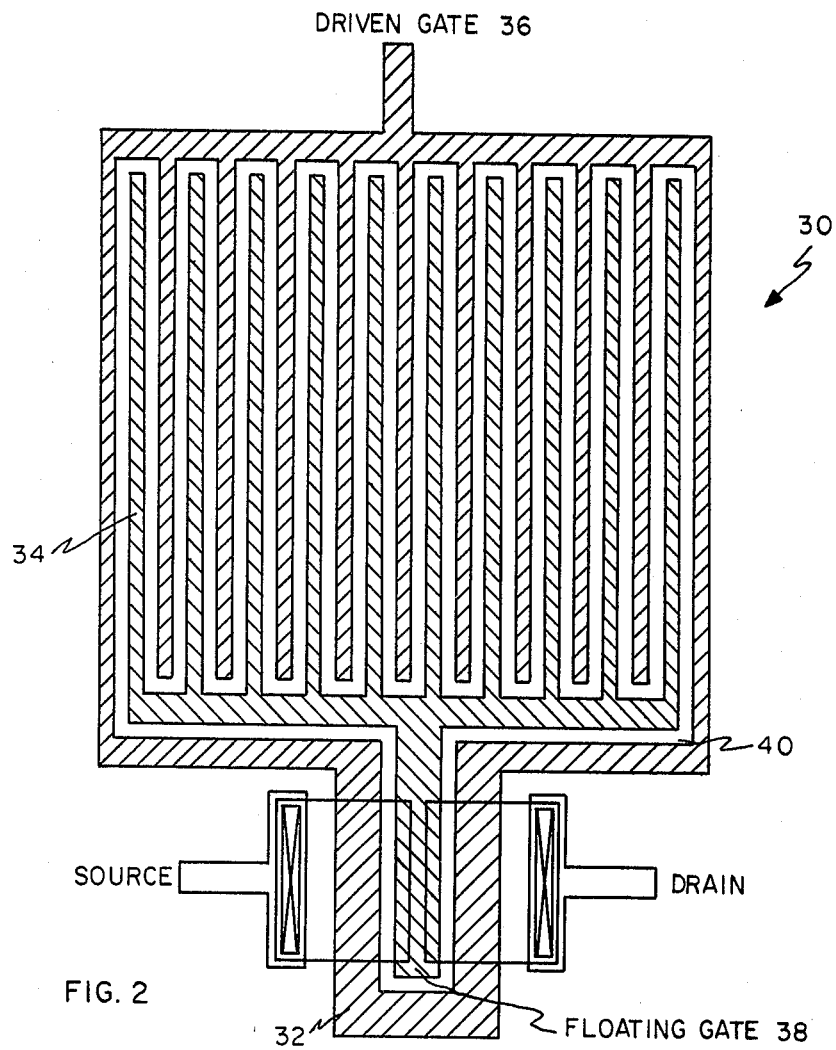
FIG. 2 is a schematic diagram of the measuring transistor component of the apparatus.
Figure 3:
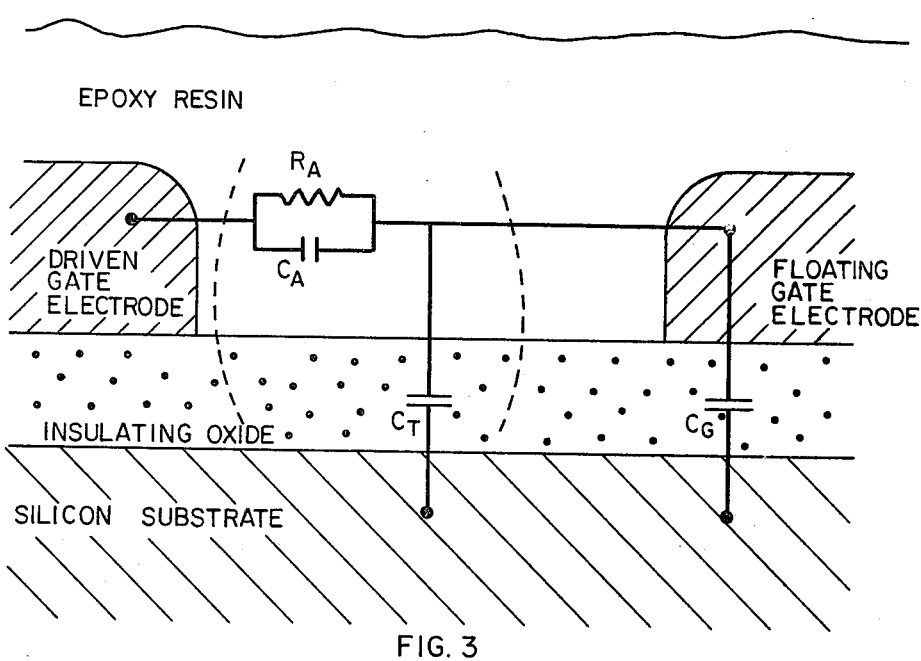
FIG. 3 is a model of the transfer function occuring at the intedigitated capacitor element of the measuring transistor.

In FIG. 2 the measuring transistor is detailed. The device 30 consists of a depletion-mode n-channel FET 32 with an interdigitated capacitive gate 34 combined into a single structure. One electrode 36 of the lock and key gate is driven externally, while the other electrode 38 ties directly to the gate of the FET.

The source and drain of the FET are available externally, just as with the CFT.

The active area for material measurements is the region between the driven gate 36 and floating gate 38. When our device is embedded in or coated with a material 40, the interdigitated capacitor is formed. The transistor 32 may be depletion-mode, and therefore may be operated with zero D.C. gate voltage bias. Additionally, the floating-gate electrode is entirely guarded by the driving electrode. An additional advantage of this lock and key adaptation is the averaging of process variations.

The transfer function for the planar interdigitated capacitor is somewhat more complicated than that for a conventional parallel plate geometry. The dependence of the amplitude and phase of the sensing gate voltage on the complex dielectric constant of the resin (permittivity $\epsilon'$, and $R_A$ is proportional to $1/\omega\epsilon''$, were $\omega$ is the angular frequency. Thus, $\tan \delta = 1/\omega R_A C_A$. $C_T$ represents the capacitance between the plane of the electrode and the ground plane beneath the silicon dioxide, and $C_G$ represents the total gate capacitance of the sensing FET and sensing electrode.

The calibration of the device on $C_T$, $C_G$, and the separation between electrodes, all of which can be controlled by device design and processing conditions. With this information, plus a single semi-empirical thickness parameter, d, there is a unique relation of $\epsilon'$ and $\epsilon''$ to the magnitude and phase of the sensing gate voltage relative to the driven gate voltage.

One solution to the transmission line problem is to define the following parameters:

$C_L$-the load capacitance of the transmission line, consisting primarily of the capacitance between the floating electrode and the substrate with the field dielectric as insulator, and also including the FET gate capacitance $C_T$-the transmission-line capacitance over which the sheet resistance and capacitance of the thin film is distributed $C_X$-the stray capacitance through the ambient between the driven-gate and floating-gate electrodes
$C_A$-the sheet capacitance of the thin film
$R_A$-the sheet resistance of the thin film
Two of the parameters of the model ($C_L$ and $C_T$) may be calculated from device dimensions. $C_A$ and $R_A$ are properties of the film (or surface), and $C_X$ is obtained from calibration measurements.

The transmission-line problem may be solved subject to the boundary conditions imposed by $C_L$ and $C_X$ to yield:

$$\frac{V_{fg}}{V_{dg}} = \frac{1 + (C_X/C_T)\alpha \sinh\alpha}{\cosh\alpha + (C_L/C_T + C_X/C_T)\alpha \sinh\alpha}$$

where $$\alpha = \left[\frac{j(C_T/C_A)}{j + (L/\omega R_A C_A)}\right]^{\frac{1}{2}}$$

In our analysis, we will assume for simplicity that only the sheet resistance $R_A$ will vary. Note that the quantities $\omega$ and $R_A$ appear in the transfer function only in the parameter d and only as a product. Thus, if one simply varies this product from a small to a large value, the entire transfer function is mapped out, regardless of whether the variation in is due to changing frequency or changing sheet resistance. If the sheet resistance of the film changes, one can return to the same magnitude and phase of the transfer function simply by changing the frequency to compensate for the sheet resistance change.

The above-solution provided a excellent model for samples in which a material was coated onto the interdigitated capacitor. Those skilled in the art can apply more complicated solutions to samples in which the device is implanted into a material.

In FIGS. 4a-4c the basic device fabrication technique is shown.

The substrate is a <100> p-type silicon wafer, with a relatively low resistivity. As in the PMOS process, the first step is the growth of a thick field oxide. This oxide can be approximately one micron thick; oxides of greater thickness require extremely long growth times, even in steam. A masking step is then performed in which holes are etched through the oxide to the silicon in the regions of the wafer where source or drain regions are desired.

An implant is now used to introduce a n-type dopant, such as arsenic, into the exposed regions of the silicon. Arsenic was chosen because of its low diffusivity as compared to phosphorous at the temperature of gate oxide growth (1100 degrees centigrade).

A layer of oxide 2500 Angstroms thick is then grown over the arsenic-doped regions. A masking step follows in which holes are etched through the oxide to the silicon in the gate and contact hole areas of the wafer. A gate oxide of approximately 1000 Angstroms is then grown over these regions.

A second ion implantation is now done, this time with phosphorous as the dopant. The implant strength is such that only the regions of the wafer under the thin gate oxide receive any impurities. This implant dopes the channel regions n-type, forming the depletion-mode devices.

A masking step in which the contact holes are opened to the silicon now takes place. The entire wafer is then coated with a layer of aluminum by evaporation. The aluminum is patterned in a final masking step to form the gates, electrodes, bonding pads, and interconnections for the devices.

Figure 5:
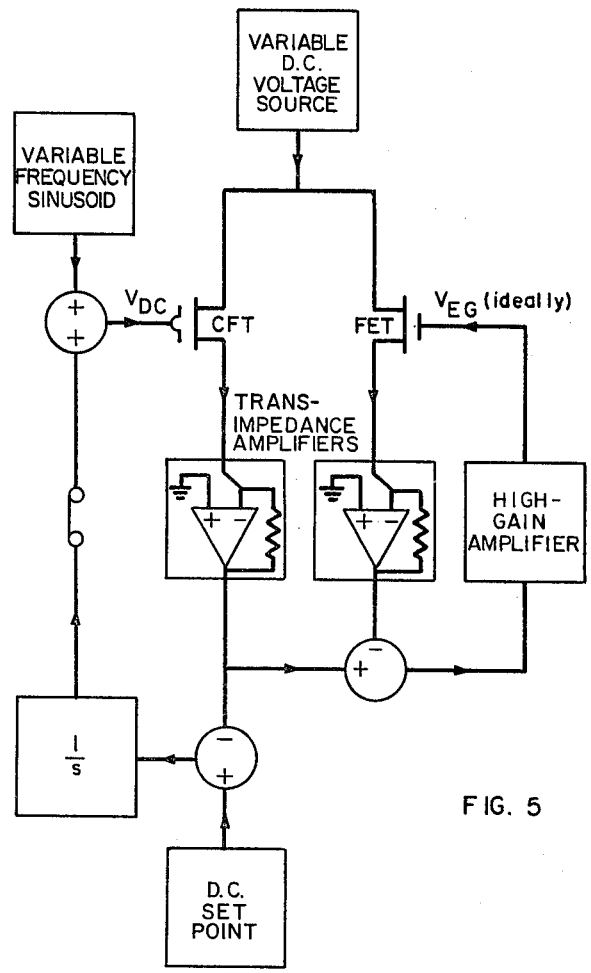
FIG. 5 is a block diagram of our measuring technique.

The block diagram of the measurement scheme is presented in FIG. 5. The technique employs our measuring transistor (also called a charge-flow transistor or CFT) a matched FET, and external circuitry. The circuit consists of two major feedback loops: a primary loop which forces FET current equal to that of the CFT, and a secondary loop which maintains the D.C. operating point of the CFT.

The drain of the CFT and matched FET are connected to a variable D.C. voltage source. The sources of the two transistors are connected to the inputs of transimpedance current amplifiers, and are thus at virtual ground. In the primary loop, the outputs of the current amplifiers are compared, and the difference is amplified by a high-gain differential amplifier. The output of this differential amplifier drives the gate of the FET, forcing both A.C. and D.C. components of the FET current to be equal to those of the CFT.

The secondary loop takes the CFT transimpedance amplifier output, and adds it to a user-selected D.C. set point. The result is integrated, and added to a variable-frequency sinusoid to provide gate drive for the CFT. This loop serves to maintain CFT D.C. current at the user-selected set point. This feature is optional, and does not function when the D.C. Level Control Switch is opened.

Given that the drain, source, and substrate voltages are the same for both the CFT and the FET, and since the drain to source currents are forced to be the same as well, the gate voltage of the FET must be equal to the floating-gate voltage of the CFT. Thus, the floating-gate voltage of the CFT can be determined indirectly simply by measuring the FET gate voltage which is supplied by the external circuitry.

As long as the CFT and FET have well matched transistor properties, the circuit will successfully subtract out all common-mode properties, and output a signal that reflects only the desired property: the voltage of the floating gate as compared to the driven gate.

Figure 6:
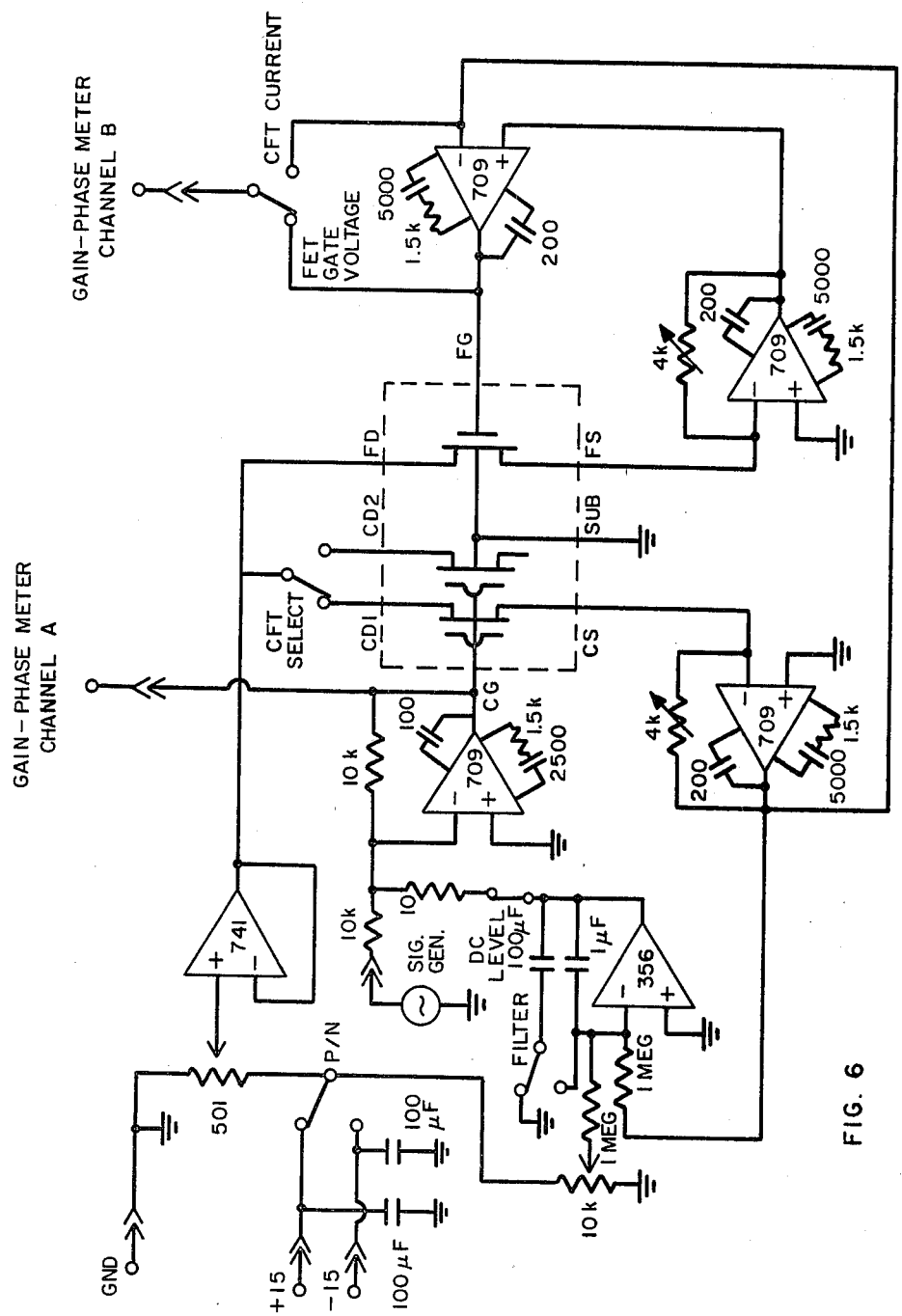
FIG. 6 is a schematic diagram of a measuring circuit.

The detailed circuit diagram is presented in FIG. 6. The circuit employs six operational amplifiers, four of which are user-compensatable for improved high-frequency response. The circuit was tested with FETs and for frequencies up to 4 kHz, the circuit responded with less than one degree of phase error.

Initial experiments were conducted on polyethylene oxide (PEO) and our devices were used to determine the moisture contents of specific samples by monitoring changes in the surface impedance of the PEO coated onto the interdigitated capacitor. The driven gate voltage and the reference voltage were simultaneously sent to a HP3575A gain-phase meter which determined the ratio of their amplitudes and relative phase shift. The digitized information was logged in real time by a HP85 desktop computer. The HP85 also controlled a HP3325A function generator, which set the frequency and amplitude of the driven gate voltage.

The results of the moisture sensing experiments correlated well with theory. All the data for dew points and frequencies fell on a single curve as predicted by the model. They showed the expected sharp drop in sheet resistance at dew points above 5° C. which corresponded to about 30 pecent relative humidity at room temperature.

Experiments on cure monitoring with our apparatus have also been conducted. Chips have been embedded into curing resins and dielectric responses measured at 10, 100 and 1000 Hz. Sharp discontinuities in gain and phase data have been observed at the resin gel point. It is believed that our apparatus and method can have utility whenever industrial factors, such as mold geometry and temperature, require in-situ measurements of material reaction rates.

What we claim is:

1. A measuring device for measuring the impedance of a material, the device comprising:
   (a) a measuring transistor comprising:
      i. a semiconductor substrate, having formed therein a source region and a drain region, the source and drain regions being situated in the substrate such that a sensitive channel region separates them from each other;
      ii. a gate insulator situated above the sensitive channel region of the substrate
      iii. a first driven gate situated far enough remote from the channel region so that charge thereon does not directly affect the channel region; and
      iv. a second, floating gate having a plurality of electrically conductive fingers proximate to, but spaced apart from, the first driven gate such that the material under measurement may fill the spaces therebetween, the floating gate being situated so that at least a portion of its electrically conductive area is situated above the gate insulator and sensitive channel region, whereby when a signal is applied to driven gate, the response of the floating gate in permitting current to flow in the channel will be dependent on the impedance of the material, and
   (b) a conventional field effect transistor of substantially identical channel dimensions and substrate composition as the measuring transistor, the two transistors being connected in differential configuration and arranged such that their drain currents are constrainted to be equal,
   (c) means to introduce a time-varying voltage on the driven gate of the measuring transistor, and
   (d) means to determine the impedence of the material by comparing the introduced voltage and the gate voltage of the conventional transistor.

2. A method of monitoring in situ the curing of resins, the method comprising:
   (a) forming a charge flow transistor suitable for monitoring, said transistor having a substrate with source and drain regions and a channel therebetween, a gate insulator above the channel, a multifingered floating gate situated at least in part over the gate insulator and channel region, and a driven gate which is spaced apart from, and surrounds, the floating gate and is remote from the channel;
   (b) applying the resin to be monitored to an active area between the driven and floating gates;
   (c) introducing a low frequency sinusoidal current to the driven gate; and
   (d) measuring the transistor response, whereby the changing response over time provides a monitor of resin curing.

* * * * *